United States Patent
Krumme

(10) Patent No.: US 7,217,351 B2
(45) Date of Patent: May 15, 2007

(54) VALVE FOR CONTROLLING FLOW OF A FLUID

(75) Inventor: John Krumme, Tahoe City, CA (US)

(73) Assignee: Beta Micropump Partners LLC, Menlo Park, CA (US)

( * ) Notice: Subject to any disclaimer, the term of this patent is extended or adjusted under 35 U.S.C. 154(b) by 767 days.

(21) Appl. No.: 10/651,835

(22) Filed: Aug. 29, 2003

(65) Prior Publication Data

US 2005/0045480 A1    Mar. 3, 2005

(51) Int. Cl.
- *G01N 27/453*    (2006.01)
- *B01L 11/00*    (2006.01)
- *F16K 31/02*    (2006.01)

(52) U.S. Cl. .................. 204/600; 422/103; 251/129.01
(58) Field of Classification Search ................ 204/450, 204/600; 251/129.01; 422/99, 100, 103
See application file for complete search history.

(56) References Cited

U.S. PATENT DOCUMENTS

| | | | |
|---|---|---|---|
| 6,019,882 A | 2/2000 | Paul et al. | |
| 6,224,728 B1 | 5/2001 | Oborny et al. | |
| 6,406,605 B1 | 6/2002 | Moles | |
| 6,782,746 B1 | 8/2004 | Hasselbrink, Jr. et al. | |
| 6,952,962 B2 * | 10/2005 | Hasselbrink et al. .......... 73/253 |
| 2002/0189947 A1 | 12/2002 | Paul et al. | |
| 2002/0195344 A1 | 12/2002 | Neyer et al. | |
| 2003/0006140 A1 | 1/2003 | Vacca et al. | |

FOREIGN PATENT DOCUMENTS

| EP | 0470743 A1 | 2/1992 |
|---|---|---|
| WO | WO 02/29106 | 4/2002 |

* cited by examiner

*Primary Examiner*—Alex Noguerola
(74) *Attorney, Agent, or Firm*—Madson & Austin

(57) ABSTRACT

A valve for controlling flow of a primary fluid in a primary flow channel comprises a valve fluid channel, and a membrane of a porous dielectric material located in the channel so as to divide the channel into an inlet part and an outlet part and so that valve fluid flowing between the inlet and outlet parts flows through the said membrane. First and second electrodes are located for electrical communication with valve fluid in the inlet and outlet parts respectively of the valve fluid channel for application of an electric potential across the membrane in order to promote electro-osmotic flow of valve fluid through the membrane. A valve member can be displaced between open and closed positions as a result of valve fluid moving in the valve fluid channel through the membrane, into or out of the outlet part of the valve fluid channel, in which the valve member causes a reduction in the capacity for flow of the primary fluid in the primary flow channel when it is in the closed position compared with when it is in the open position.

15 Claims, 9 Drawing Sheets

VALVE FOR CONTROLLING FLOW OF A FLUID

This invention relates to a valve for controlling flow of a fluid in a flow channel, and to a pump for controlling flow of a fluid in a flow channel.

The flow of fluids through conduits can be controlled using components such as pumps and valves. Pumps and valves can operate to control parameters such as flow rate; adjustment of relative flow rates of constituents in a mixture can be used to vary the composition of the mixture.

Accurate control of flow of a fluid can be important in many medical applications, for example in drug delivery and in the modulation of body fluid drainage. Devices in which flow control is important include pumps for dispensing drugs such as insulin and opiates, and hydrocephalus shunts for drainage of spinal fluids.

Accurate control over the flow of drugs and fluids in medical applications can help to minimise complications in the patient treatment, especially if controlled quantities of drugs can be supplied locally to an affected site. Accurate control can help to optimise efficacy of an administered drug. The use of controlled quantities can also help to minimise wastage of drugs, and therefore to minimise treatment costs. An implanted device for controlling flow of drugs can help to ensure compliance with prescribed drug administration regime by eliminating patient dependence on operation of the device.

Accurate and localised control of a drug can be facilitated by means of implanted control devices. U.S. Pat. No. 6,287,295 relates to an implantable device which relies on a semipermeable membrane to control the rate of drug delivery. However, once implanted, the rate of flow of drug through the membrane cannot readily be adjusted.

Electro-osmotic flow controllers apply a potential difference to liquid on opposite sides of a semi-permeable membrane made of a dielectric material. Provided that the liquid is able to yield a high zeta potential with respect to the porous dielectric material of the membrane, the application of the potential difference leads to transmission of charged species, possibly together with solvent (for example which solvates the charged species or as bulk solvent by viscous drag), through the membrane. This technology can be used to control the rate at which a liquid is supplied, for example under pressure which is generated by means of a pump. The technology, including amongst other things details of the materials which can be used for the membrane and as the liquid which is transmitted across the membrane, is discussed in detail in US-A-2002/189947. Subject matter disclosed in that document is incorporated in the specification of the present application by this reference.

The present invention provides a valve for controlling flow of a primary fluid in a primary flow channel, including a valve member which can be displaced between open and closed positions as a result of electro-osmotic flow of valve fluid, in which the valve member causes flow of the primary fluid in the primary flow channel to be interrupted when it is in the closed position, and allows flow of the primary fluid in the primary flow channel when it is in the open position.

Accordingly, in one aspect, the invention provides a valve for controlling flow of a primary fluid in a primary flow channel, which comprises:

a. a valve fluid channel, b. a membrane of a porous dielectric material located in the channel so as to divide the channel into an inlet part and an outlet part and so that valve fluid flowing between the inlet and outlet parts flows through the said membrane, c. first and second electrodes located for electrical communication with valve fluid in the inlet and outlet parts respectively of the valve fluid channel for application of an electric potential across the membrane in order to promote electro-osmotic flow of valve fluid through the membrane, d. a valve member which can be displaced between open and closed positions as a result of valve fluid moving in the valve fluid channel through the membrane, into or out of the outlet part of the valve fluid channel, in which the valve member causes a reduction in the capacity for flow of the primary fluid in the primary flow channel when it is in the closed position compared with when it is in the open position.

The valve of the present invention has the advantage that it can be controlled by applying or changing the potential difference across the membrane, allowing control of the rate or direction of flow (or both) of fluid through the membrane. This can be a particular advantage when access to the valve is restricted when it is in use. In particular, this can be the case when the valve has been implanted in a human or animal body. However, it is also relevant when the valve is inaccessible in some other way, for example when the valve is located within an enclosure (for example a casing for fluid supply apparatus) or at a location which is remote from an operator when wireless or wired communication signals (for example telecommunications signals) can be used to cause a change in the applied potential difference.

The valve of the invention relies on electro-osmotic flow of the valve fluid through the membrane of porous dielectric material. This effect arises when a liquid is in contact with a dielectric solid and the natural electrochemistry of the interaction produces a thin layer of net charge density in the liquid in the region of the interface. An applied electric field which includes a component perpendicular to the interface causes motion of the net charge. Viscous action imparts motion to the adjacent liquid which remains neutral. Accordingly, in the valve fluid channel of the valve of the invention, a potential difference applied across the membrane by means of the first and second electrodes produces electro-osmotic flow of liquid through the membrane.

Electro-osmotic flow may be generated using a wide variety of fluids and dielectric materials. Indeed, it is an advantage of the present invention that the valve fluid can be isolated from the primary fluid so that an optimum fluid can be selected for operating the valve without reference to the particular requirements or nature of the primary fluid. The valve fluid should provide conditions that yield a high zeta potential with respect to the porous dielectric material. The fluid might be a pure fluid or a mixture of pure fluids. The fluid might have added to it a conducting species, especially a material which dissolves in the fluid to form ions. Preferably, the or each pure fluid should have a high dielectric constant (for example, between about 5 and 100 relative units), low dynamic viscosity (for example, between about 0.1 and 2 centipoise) and low conductivity (for example, between about $10^{-4}$ and $10^{-14}$ mho·m$^{-1}$).

The valve fluid can include at least one additive to control the pH of the fluid. The valve fluid can include at least one additive to control the ionic strength of the fluid. Additives should preferably dissolve completely in the fluid. The kind and concentration of additives should preferably be such as to enhance or to optimise the zeta potential under the conditions imposed by the size of the pores in the porous dielectric medium.

The degree of ionization of the surface sites depends on the pH of the fluid. In most cases there is a pH at which the surface is net neutral and hence the zeta potential is zero. The zeta potential reaches a maximum value for pH values significantly above (for acidic surface sites) or pH values significantly below (for basic surface sites) the pH value at which the surface is net neutral. Ionisable surface sites can be added to a material by chemical reaction or grafting, or induced by creation of reactive surface chemistry or creation of defects via plasma or radiation treatment.

Examples of fluids which can be used in the valve fluid include water, cyclic carbonates, methanol, ethanol, 1-propanol, 2-propanol, 1-butanol, 1-pentanol, 1-hexanol, 1-heptanol, benzyl alcohol, nitromethane, nitrobenzene, butanone, dimethoxymethane, dimethylacetamide, dioxane, p-dioxane, acetonitrile, formamide, tetrahydrofuran, dimethyl formamide, acetone, acetic acid, triethylamine, dichloromethane, ethylene glycol, dimethylsulphoxide, ammonium acetate.

The valve fluid can include additives which can affect the zeta potential. Ionic species can have the opposite charge sign to the zeta potential. Ionic species can have the same charge sign as the zeta potential. Preferably, ionic species which are included in the valve fluid are monovalent. Species which ionise fully can be used to adjust the ionic strength of the fluid. Species which ionise partially can be used to adjust the pH of the fluid. Examples of useful ionic and buffering additives include alkali-halide salts, mineral acids and bases, organic acids and bases, phosphates, borates, acetates, citrates, malates, formates, carbonates, chlorates, nitrates, sulphates and sulphites, nitrates and nitrites, ammonium-, methylammonium-, ethylammonium-, propylammonium-salts, BIS, MES, TRIS, TES, HEPES, and TEA.

Preferably, the materials of the valve fluid and the porous dielectric material are such that the zeta potential is at least about 1 mV, especially at least about 30 mV. Generally, the zeta potential will be not more than about 150 mV, for example not more than about 120 mV. The zeta potential may be either positive or negative in sign. Factors affecting the sign and magnitude of the zeta potential include the dielectric constant of the fluid, the pH of the fluid, the ionic strength of the fluid, and the type of ions in the fluid.

The surface of the porous dielectric material will generally be required to exhibits acidic or basic sites that become ionised in the presence of the valve fluid. These ionisable surface sites may be native to the material or may be the result of adsorption of some species onto the surface material. Examples of materials which are inherently capable of creating ionised sites include silica (which exhibits acidic surface sites), alumina (amphoteric) which can exhibit basic or acidic surface sites, polyamides such as a Nylon (which exhibits both acidic (carboxyl) and basic (amine) surface sites—zwitterionic). The sign of the zeta potential is the same as the sign of the net surface charge.

A membrane which is not capable inherently of creating ionised sites (for example a polyolefin, such as polyethylene or polypropylene or mixtures thereof) can be modified by means of additives such as ionic surfactants. When such a membrane is exposed to an aqueous solution containing certain ionic surfactants (for example sodium dodecyl sulphate), the hydrophobic tail of the surfactant adsorbs to the polymer, and the charged end of the surfactant then appears as a charge site on the surface.

The dielectric material of the membrane is selected for properties of high zeta potential, the sign of the zeta potential, insolubility and stability in the valve fluid, low electrical conductivity, and sufficient mechanical strength. Examples of dielectric materials which can be used in the membrane include ceramic oxides, glasses, ceramic nitrides, certain polymers, carbides and silicides.

Examples of suitable oxide materials include silica, alumina, titania, zirconia, cerium oxide, lanthanum oxide, yttrium oxide, hafnium oxide, magnesium oxide, and tantalum oxide. These oxides may be amorphous or glassy or crystalline and may be combined in mixtures having other minor oxide components.

Examples of suitable nitride materials include silicon nitride, boron nitride, and aluminium nitride.

Examples of suitable polymers include sulphonated fluoropolymers (such as that sold under the trade mark Nafion), polysulphones, polyethersulphones, polycarbonates, polyacrylonitriles, polyvinylidene fluorides, polyamides (Nylon), silicone elastomers and polymethacrylates.

Certain semiconductors might be used in the membrane, such as carbides (for example titanium carbide) and silicides (for example germanium silicide).

The geometry of the pores in the membrane will affect the performance of the valve, including the length and transverse dimension, and the tortuosity. Details of the formation of suitably porous membranes and design parameters are known.

Preferably, the valve fluid channel comprises a tubular member in which the membrane is located to divide the tubular member into two parts which are spaced apart along the length of the tubular member. The tubular member will often have a generally constant cross-section along at least a substantial part of its length, especially for ease of manufacture. Frequently, the tubular member will have a rounded shape (especially a circular shape) when viewed in cross-section along the axis of the member. However, other shapes are envisaged, such as square or rectangular.

The tubular member of the valve fluid channel should have sufficient mechanical strength to withstand the pressures which are generated within it. The material should be compatible with and impermeable to the fluids with which it will come into contact when in use.

The membrane can be fabricated as a separate part and then mounted in a tubular member or in a sheet. The membrane can be fabricated in situ in a tubular member or sheet.

Other details of the materials, construction, operation of devices which exhibit electro-osmotic flow properties are known, for example as disclosed in US-A-2002/189947 and documents referred to therein.

The valve fluid channel can be defined by the membrane of the porous dielectric material, with inlet and outlet parts on respective sides thereof which are defined by expandable inlet and outlet diaphragms which are bonded to the membrane on opposite sides thereof. The membrane can be provided in a sheet in which the porous dielectric properties which are required for the electro-osmotic effect to be exhibited are provided in a localised region. The inlet and outlet diaphragms can then be bonded to the sheet at locations outside the said localised region. A valve in which the valve fluid channel is defined by a membrane with inner and outer diaphragms in this way has the advantage that the valve has a lower profile by virtue of smaller thickness, compared with a valve in which the valve fluid channel is provided by a tubular member.

A further advantage of the valve of the present invention is that the primary fluid whose flow is controlled by the valve need not have the characteristics which are necessary for electro-osmotic flow effects to be demonstrated by it. Accordingly, the valve can be used to control the flow of fluids which are not capable in normal operating conditions of demonstrating a zeta potential with respect to the dielectric material of the membrane. The valve can also be used to control the flow of fluids which are too viscous to be able to flow through a membrane of a suitable dielectric material. Instead of relying on the primary fluid to demonstrate electro-osmotic flow effects, these effects can be provided by a fluid which is different from the primary fluid, referred to herein as the valve fluid. Electro-osmotic flow of the valve fluid causes displacement of the valve member which can then act mechanically to control the capacity of the primary fluid channel, for example to affect the rate of flow of the primary fluid along that channel or to affect the volume of the channel for the primary fluid.

The outlet part of the valve fluid channel will generally be a closed chamber so that fluid flowing into or out of the outlet part flows through the membrane. Accordingly, flow of fluid into or out of the outlet part of the valve fluid channel can cause the volume of the outlet part of the valve fluid channel to change, for example by deformation (such as inward or outward deformation) of at least a part of the wall of the outlet part. For example, the deformation can be outward deformation when the valve member acts against a primary flow channel which is located externally of the valve fluid channel. The deformation can be inward deformation when the primary flow channel is provided a compressible tube which extends through the outlet part of the valve fluid channel: the compressible tube then defines an internal wall of the outlet part of the valve fluid channel.

Preferably, at least part of an external wall of the outlet part of the valve fluid channel is defined by a diaphragm which can expand. The construction of the diaphragm can be such that it expands in the manner of a balloon when the material of the diaphragm is resiliently deformable.

A diaphragm which defines part (or all) of the wall of the outlet part of the valve fluid channel can be provided by a resiliently deformable material. For example, an elastomeric material can be used. Suitable elastomeric materials will be selected according to the fluids with which the valve will come into contact when in use. Examples might include certain silicones, ethylene-propylene copolymers, and urethanes. Characteristics of a deformable material for the diaphragm, such as its thickness and other factors which affect its deformability, will be selected according to the intended application for the valve, including the pressures to which it will be exposed. The characteristics of certain deformable polymeric materials can be optimised by crosslinking.

A diaphragm which is formed from a resiliently deformable material can be provided on a tubular valve fluid channel which is relatively non-deformable (such that its dimensions remain substantially unaltered during normal operation of the valve). The diaphragm can be sealed to the surface of the tubular fluid channel, with openings in the tubular fluid channel for the valve fluid to flow into the space defined by the diaphragm. For example, one or more openings can be provided in the longitudinal side wall of the tubular fluid channel, or one or more openings can be provided in the end wall of the tubular fluid channel.

The diaphragm can be provided by expandable bellows. Expandable bellows are able to accommodate a change in the volume of the outlet part of the valve fluid channel by a change in their shape, with or without significant deformation of the material of the diaphragm. For example, the diaphragm could have a compact configuration in which it is folded when the volume of the valve fluid channel is relatively small, and an extended configuration in which the folds are opened out when the volume of the valve fluid channel is greater.

Preferably, the valve fluid channel includes a tubular member which has a side wall and an end wall, and the diaphragm is located on the side wall so that the channel can expand transversely in response to an increase in fluid pressure in the outlet part of the valve fluid channel. A diaphragm which is provided on the side wall of the valve fluid channel will be in communication with the interior of the said channel, preferably by means of one or more openings in the wall of the channel, especially in the side wall thereof. The diaphragm should be sealed to the valve fluid channel to prevent loss of valve fluid.

The outlet part of the valve fluid channel can be located at least partially within the primary flow channel, especially when it includes a tubular member, so that an increase in fluid pressure in the outlet part of the valve fluid channel causes the outlet part diaphragm to expand (for example by deformation of a resiliently deformable material, or by expansion of bellows, or by a combination of the two) towards the wall of the primary flow channel to control the capacity of the primary fluid channel. Preferably, the diaphragm expands transversely relative to the valve fluid channel, towards the wall of the primary flow channel. This arrangement finds particular application when the diaphragm is located on the side wall of the valve fluid channel and expands transversely in response to an increase in fluid pressure in the outlet part of the said channel. The diaphragm can then close at least partially the space between the internal wall of the primary flow channel and the valve fluid channel to restrict or to stop flow of the primary fluid through that space.

When the valve fluid channel includes a tubular member which has a side wall and an end wall, the diaphragm can be located at the end wall so that the channel can expand longitudinally in response to an increase in fluid pressure in the outlet part of the valve fluid channel. This arrangement finds application when the primary flow channel includes an orifice through which the primary fluid can flow, and the end wall of the valve fluid channel is located adjacent to the orifice. An increase in fluid pressure in the outlet part of the valve fluid channel can cause the diaphragm to expand (for example by deformation of a resiliently deformable material, or by expansion of bellows, or by a combination of the two) towards the orifice to close it at least partially against flow of the primary fluid. This arrangement is suitable for use of the construction of valve discussed above in which inlet and outlet diaphragms are fastened to a sheet of which a localised region provides the membrane of porous dielectric material.

A diaphragm can be arranged as a balloon which is fastened to a surface of the valve fluid channel, especially when the valve fluid channel includes a tubular member. For example, the diaphragm can be provided as an envelope on and around the end of the tubular member of a valve fluid channel, fastened to the external surface of the member.

The valve member can include a mandrel which is mounted on the diaphragm so that it is displaced when the diaphragm expands in response to an increase in fluid pressure in the outlet part of the valve fluid channel. This can provide for more accurate sealing of an orifice to close it against fluid flow for example by suitable matching of the shape of the end of the mandrel with the shape of the orifice. A mandrel will commonly be made from a relatively rigid material so that it retains its shape, although it can have an outer surface of a deformable material to provide compliance with the shape of the primary flow channel, especially when the mandrel is intended to fit into an orifice or other profiled recess.

It is an advantage of the use of an electro-osmotic flow device in the present invention that precise control over the rate of flow of primary fluid is possible. The device can be configured so that the pressure that is generated in the outlet part of the valve fluid channel increases approximately linearly with the potential difference across the membrane. A device can be configured so that the pressure in the outlet part is about 400 kPa when the potential difference across the membrane is about 18 volts.

The primary flow channel can comprise a tube which can be compressed transversely so as to reduce the cross-sectional area thereof and its capacity. Such a reduction in area can result in a reduction in the rate of flow of fluid through the primary flow channel. It can also be used to cause a reduction in the volume of the primary flow channel that is available for the primary fluid, especially by compressing it over a significant length. The length over which the tube is compressed can be greater than is necessary simply to close the tube to flow of fluid. This can be useful when the valve is used as a part of a pump as discussed in more detail below.

A compressible tube can be compressed as a result of being located relative to the valve fluid channel so that it is compressed by the action against it of the diaphragm when it expands in response to an increase in fluid pressure in the outlet part of the valve fluid channel. It can be particularly preferred for the valve member to include a mandrel which is mounted on the diaphragm so that it is displaced when the diaphragm expands, into contact with the compressible tube. The compressible tube can be located in a chamber in which the pressure can be changed as a result of causing the valve fluid to flow between the inlet and outlet sides of the valve fluid channel, especially by having the chamber in fluid communication with the outlet side of the valve fluid channel and by causing fluid to flow into the chamber.

The valve member in the valve of the invention can be provided by a compressible tube which forms part of the primary flow channel, the compressible tube being located within a chamber which is in fluid communication with the outlet part of the valve fluid channel so that an increase in fluid pressure in the said chamber as a result of flow of valve fluid into the outlet part of the valve fluid channel can cause compression of the compressible tube, to reduce the flow of the primary fluid through the compressible tube and to reduce the volume of the compressible tube.

It can be preferred for the inlet part of the valve fluid channel to be a closed chamber so that fluid flowing into or out of the inlet part flows through the membrane. In this way, the valve fluid is retained within the valve fluid channel and is not able to mix with the fluid in the primary flow channel. This allows the valve fluid to be selected to optimise the electro-osmotic flow characteristics through the membrane component of the valve, independent of the characteristics of the primary fluid.

However, when the primary fluid is able of exhibiting electro-osmotic flow when subjected to a potential difference across a membrane of a porous dielectric material, the inlet part of the valve fluid channel can be arranged in communication with the primary flow channel.

The valve of the invention can include a valve member housing in which the valve member can move between its open and closed positions. The valve member can be made to move between its open and closed positions as a result of changes in pressure in the valve fluid resulting from flow of valve fluid through the membrane. The valve member housing can have a housing inlet and a housing outlet which communicate with the primary flow channel so that primary fluid flowing along the primary flow channel flows through the valve member housing, through the said housing inlet and housing outlet. When the valve member is in its closed position, the capacity of the primary flow channel for flow of the primary fluid is reduced compared with when the valve member is in its open position. This can involve a reduction in the cross-sectional area of the primary flow channel (and therefore also a reduction of its volume). The primary flow channel can be completely closed against flow of primary fluid or just partially closed, when the valve member is in the closed position.

The valve member can provide a flow path for the primary fluid to flow through the valve member housing, which can be aligned with the housing inlet and the housing outlet when the valve member is in the open position.

The primary flow channel can communicate with the valve member housing so that primary fluid flowing along the primary flow channel flows through the valve member housing, over, around or through the valve member. Preferably, the direction of flow of primary fluid through the valve member housing is generally transverse to the direction in which the valve member moves, or shuttles, between its open and closed positions. For example, when the valve member moves along a shuttle axis, the housing inlet and the housing inlet are each provided in a wall of the housing which extends generally parallel to the shuttle axis. It can be especially preferred for the housing inlet and outlet to be located opposite to one another. However, other arrangements are envisaged, according to the design of the flow path over, around or through the valve member. For example, the flow path can be defined by a region of the valve member with a reduced cross-section so that the primary fluid flows over the surface of the valve member. The flow path can be defined by an aperture extending through the valve member so that the fluid flows through the valve member.

The flow of the primary fluid through the valve member transversely to the direction in which the valve member moves has the advantage that the valve member is not subject to pressure differences in the primary flow channel, between the valve member housing inlet and the valve member housing outlet.

Preferably, the valve member is a close fit within the valve member housing so that a seal is formed between facing surfaces of the valve member and the housing to minimise mixing of the primary fluid and the valve fluid. Techniques for forming a sliding seal of this general kind are known, including details of the tolerances which are necessary to provide a seal while still allowing the shuttle valve member to move within the housing.

Preferably, the valve member comprises a first part which is a close fit in the housing so that fluid cannot readily flow through the housing between the first part of the valve member and the adjacent internal surface of the housing, and a second part which has a reduced cross-section compared with that of the first part, allowing flow of fluid through the housing around the second part of the valve member. It will generally be preferred for the cross-sectional shape of the first and second parts of the valve member to be similar, with the area of the second part smaller than that of the first part.

For example, when the cross-sections of the housing and the first part of the valve member are both rounded, especially circular, the cross-section of the second part of the valve member is preferably also similarly rounded, especially circular, so that fluid can flow past the valve member around the second part thereof. However, non-circular cross-sections can be used, for example oval or rectangular. The use of non-circular a cross-section for the housing and the valve part has the advantage that alignment of a bore in the valve member and inlet and outlet holes in the valve member housing is maintained.

Preferably, the shuttle valve member housing has a first end towards which it moves when moving towards its open position from its closed position and an opposite second end towards which the valve member moves when moving towards its closed position from its open position. Preferably, the valve member housing has a first opening at or towards the first end thereof which communicates with the inlet part of the valve fluid channel and a second opening at or towards the second end thereof which communicates with the outlet part of the valve fluid channel. This construction allows latching of the valve member in a desired position by adjustment of the potential difference across the membrane. The valve member can be driven through the housing reversibly by appropriately changing the polarity of the potential difference across the membrane. The valve member can effectively be latched in a desired position without the application of a potential difference while the direction of flow of the primary fluid is generally perpendicular to the direction in which the valve member moves.

One or both of the valve housing inlet and the valve housing outlet can be located in a wall towards which or away from which the valve member moves between the open and closed positions. For example, one of the inlet and the outlet can be located in a wall which extends parallel to the movement of the valve member, and the other can be provided in an end wall. The opening in the wall which is parallel to the movement of the valve member can be occluded by the valve member when in the closed position, and partially or completely opened when the valve member is in the open position.

The performance characteristics of valves of the invention which use a housing for a valve member can be changed by appropriate selection of the dimensions of the valve housing and the valve member. Parameters which can be changed include the distance through which the valve member moves between the open and closed positions of the valve (the "stroke"), and the cross-sectional area of the housing (which will be approximately the same as the valve member). A relatively short stroke, often in combination with a relatively large cross-sectional area, can have the advantage allowing larger forces to be generated to move the valve member between its open and closed positions. This can be appropriate when the fluid in the primary channel is at high pressure. It can also facilitate fast operation of the valve. A relatively long stroke can have the advantage of allowing modulation of the flow of primary fluid through the valve.

The dimensions for a shuttle valve according to the invention will be selected according to the intended application and the space which will be available to accommodate it, and also according to the quantity of the primary fluid that is required to flow through the valve when in use and the pressure of that fluid. The shuttle valve member can have a transverse dimension (which will be a diameter when the valve member has a circular cross-section) of at least about 0.5 mm, for example at least about 1.0 mm or at least about 2.0 mm. For many applications, the transverse dimension will be not more than about 5.0 mm, for example not more than about 4.0 mm or not more than about 3.0 mm. For some applications, a smaller shuttle valve member can be used, for example with a transverse dimension of not more than 1.0 mm, preferably not more than 0.5 mm, especially not more than about 0.1 mm.

The materials used to make the shuttle valve member and the valve member housing will be selected to be inert to liquids with which they come into contact when the valve is in use, wear resistance, ease of manufacture (to acceptable tolerances), low friction. It can be convenient to form the housing from a polymeric material, for example a polyolefin or a polycarbonate. This has the advantage of being capable of manufacture using moulding techniques. It also means that connections can be formed reliably to one or both of the inlet and outlet parts of the valve fluid channel. The shuttle can be formed from a metal, for example a stainless steel. Losses due to friction in metal-polymer combinations are low. The valve of the invention can be manufactured from silicon based materials, for example using semi-conductor wafer manufacturing methods.

The present invention provides a composite valve for controlling flow of a primary fluid, which includes a primary valve comprising a valve fluid channel, a membrane of a porous dielectric material, first and second electrodes and a valve member, as described generally above, and additionally a latching valve comprising a shuttle valve member as described above.

The primary flow channel can include internal valves which control the direction and rate of flow of liquid within it. A one-way internal valve can be positioned in the tube on each side of a valve according to the invention which can then function as a pump driver in a fluid pump. Preferably, the primary flow channel is provided at least in part by a compressible tube. The one-way internal valve which is upstream of the driver valve can admit fluid to flow as far as the downstream one-way internal valve. Actuation of the driver valve causes liquid within the compressible tube to be discharged through the downstream valve which opens due to the increased internal pressure within the compressible tube.

The valve of the invention can include means for biasing the valve member towards a preferred position, which might be, for example the position in which the valve is open to flow of the primary fluid, or the position in which the valve is closed to flow of the primary fluid. The provision of biasing means can provide for safety feature for the event, for example, that the valve loses power or some other failure. The biasing means can be provided by, for example, a spring member, which acts on the valve member and can be deformed resiliently when the valve member moves in the normal operation of the valve.

Accordingly, in another aspect, the invention provides a pump for controlling flow of a primary fluid in a primary flow channel, which comprises:

a. a driver valve comprising:

i. a valve fluid channel, ii. a membrane of a porous dielectric material located in the channel so as to divide the channel into an inlet part and an outlet part and so that valve fluid flowing between the inlet and outlet parts flows through the said membrane, iii. first and second electrodes located for electrical communication with valve fluid in the inlet and outlet parts respectively of the valve fluid channel for application of an electric potential across the membrane in order to promote electro-osmotic flow of valve fluid through the membrane, iv. a valve member which can be displaced between open and closed positions as a result of valve fluid moving in the valve fluid channel through the membrane, into or out of the outlet part of the valve fluid channel, in which the valve member causes a reduction in the volume of the primary flow channel when it is in the closed position compared with when it is in the open position, b. an inlet valve located upstream of the driver valve, for controlling flow of primary fluid into the primary flow channel where it is acted on by the driver valve, and c. an outlet valve located downstream of the driver valve, for controlling release of primary fluid from the primary flow channel where it is acted on by the driver valve.

Features of the valve of the invention which are discussed in this document can be incorporated in the driver valve of the pump of the invention.

Preferably, the pump can preferably include a latching valve to control flow of the valve fluid in the valve fluid channel. The latching valve can be a shuttle valve according to this invention. Preferably, one or each of the inlet valve and the outlet valve can be a valve according to this invention. Preferably, one or each of the inlet valve and the outlet valve includes a latching valve to control the flow of valve fluid in the respective valve fluid channel. The or each latching valve can be a shuttle valve according to this invention.

Embodiments of the invention will now be described by way of example with reference to the accompanying drawings, in which:

FIG. 11b is an isometric view of the pump shown in FIG. 11a.

Figure 1A:
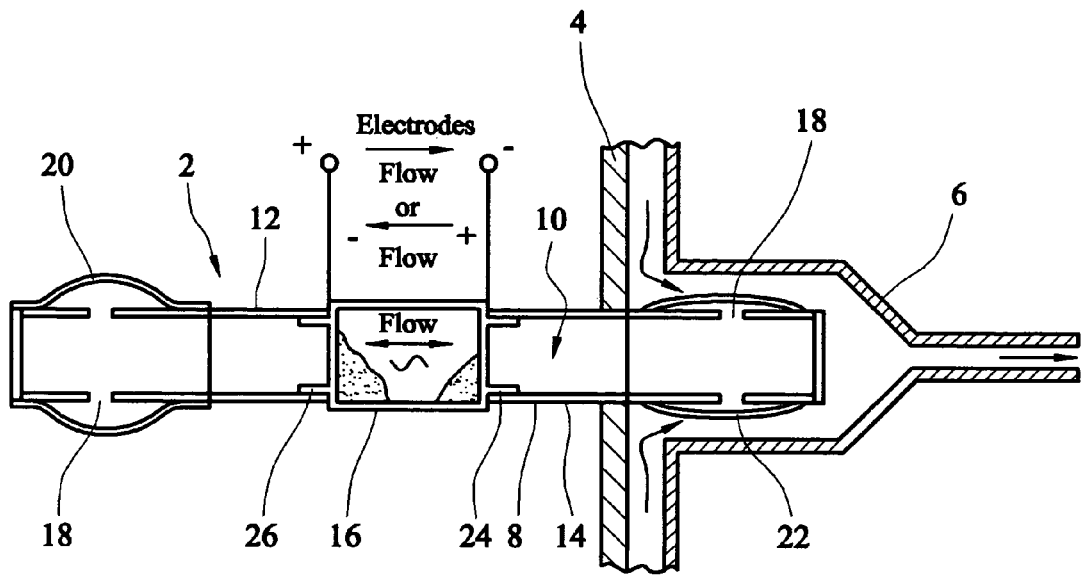
FIG. 1a is a side view of a valve according to the invention which is open to allow flow of primary fluid.

Referring to the drawings, FIG. 1 shows a valve 2 for controlling flow of a primary fluid in a primary flow channel. The primary flow channel is defined by a baffle 4 and a conduit wall 6.

The valve includes a channel 8 which contains a quantity of a valve fluid 10. The valve fluid channel 8 comprises two tubular parts 12, 14, located on opposite sides of a membrane 16 which is formed from a porous dielectric material. The porous dielectric material can be, for example, an aluminium oxide ceramic which has been rendered porous. Details of suitable materials, and of techniques for rendering them porous, are known. Each of the tubes 12, 14 is bonded to the membrane 16 by adhesive bonding. Adhesive can be provided between the external surface is of lugs on the membrane which extend into the tubes, and the internal surfaces of the tubes.

Each of the tubes 12, 14 is formed from a rigid polymeric material which is compatible with the valve fluid and the primary fluid. Examples of materials from which the tubes might be formed include metals (especially stainless steel) and polymers (for example, polyamides, polyesters, polycarbonates, polyolefins etc). The thickness of the tube should be sufficient to ensure that the tube does not distort in use when subjected to normal operating pressures of the valve.

Each of the tubes has a constant cross section. Each of them is closed at its free end (remote from the membrane). The tubes can be closed by bonding a plain wall to the tube section, for example using an adhesive, or by welding.

Each of the tubes has a series of holes formed in it towards its free end. For example, each of the tubes might have six holes formed in it, arrayed uniformly around its circumference.

Each of the tubes has a tubular sleeve 20, 22 bonded to its external surface so as to cover the holes 18 and to provide a fluid-tight seal to prevent loss of valve fluid. Each of the sleeves is formed from a resiliently deformable elastomer which can stretch to accommodate valve fluid in the space between it and the external surface of the respected tube.

Each of the tubes 12, 14 includes an electrode 24, 26 which is located on the respective face of the membrane, 16. The electrodes are arranged for connection to a DC power source.

The valve fluid channel 8, comprising the tubes 12, 14 and the membrane 16 is mounted with respect to the baffle 4 so that the tube 14 extends through the baffle and is sealed to it. The seal prevents flow of primary fluid through the baffle from the primary flow channel. Applying a potential difference across the membrane of porous material 16, by means of the electrodes 24, 26 causes the valve fluid 10 to flow between the inlet tube 12 of the valve fluid channel and the outlet tube 14. The volume of fluid within the valve fluid channel (including that between the external surfaces of the tubes 12, 14 and the tubular diaphragm sleeves, 20, 22) remains constant. The application and the potential difference across the membrane 16 of dielectric material determines the distribution of liquid between the inlet tube 12 and the outlet tube 14. Changes in the volume of liquid in either of these tubes is accommodated by expansion of the space between the tubular diaphragm sleeves 20, 22 and the adjacent external surface of the respective tube.

In FIG. 1a, there is relatively more of the valve fluid on the inlet side 12 of the membrane 16, compared with the volume of fluid on the outlet side 14. As a result, the tubular membrane diaphragm 22 is not stretched, and has a low profile close to the surface of the tube 14. In contrast, the tubular sleeve membrane 22 on the inlet side is expanded to accommodate valve fluid. This is as a result of the application of a potential difference across the electrodes 24, 26.

With the tubular diaphragm sleeve 22 contracted, primary fluid is able to flow through the primary flow channel, in the space between the external wall 6 of the flow channel and the valve 2. This is as shown in FIG. 1a.

Figure 1B:
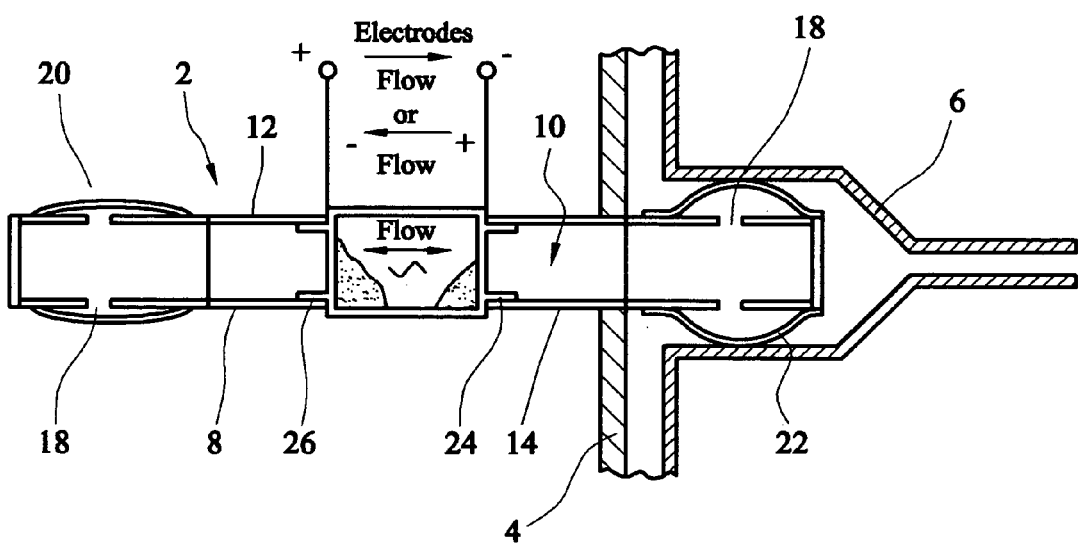
FIG. 1b is a side view of the valve shown in FIG. 1a which is closed to prevent flow of primary fluid.

In FIG. 1b, the potential difference applied across the electrodes 24, 26 is reversed, causing valve fluid to flow from the inlet side 12 of the membrane 16 to the outlet side 14. This allows the tubular diaphragm sleeve 20 on the inlet side to contract, while the tubular membrane diaphragm 22 on the outlet side expands to accommodate migrating valve fluid. The tubular diaphragm sleeve 22 on the outlet side expands until it contacts the internal surface of the wall 6 of the primary flow conduit, to form a seal between it and the valve 2. This cuts off the flow of primary fluid in the primary flow conduit. The valve is therefore closed.

The valve can revert to the open configuration shown in FIG. 1a from the closed configuration shown in FIG. 1b by once again reversing the potential difference across the electrodes 24, 26.

FIG. 2 shows another construction of valve in which the membrane of porous dielectric material 50 is formed as part of a baffle 52. As in FIG. 1, the baffle together with a wall 54 defines a flow conduit 56 for a primary fluid.

A valve fluid channel is provided, defined by the membrane 50 of the porous dielectric material and spaces on each side of the baffle 52 which are defined by deformable diaphragm seals 58, 60.

Electrodes 62, 64 are provided on opposite sides of the baffle 52, so that they are in contact with valve fluid contained in the spaces between the baffle 52 and the respective diaphragm seal 58, 60.

The application of a potential difference across the membrane 50 by means of the electrodes 62, 64 can cause valve fluid to move from the inlet side of the membrane (defined by the diaphragm seal 58) to the outlet side (defined by the diaphragm seal 60).

Figure 2B:
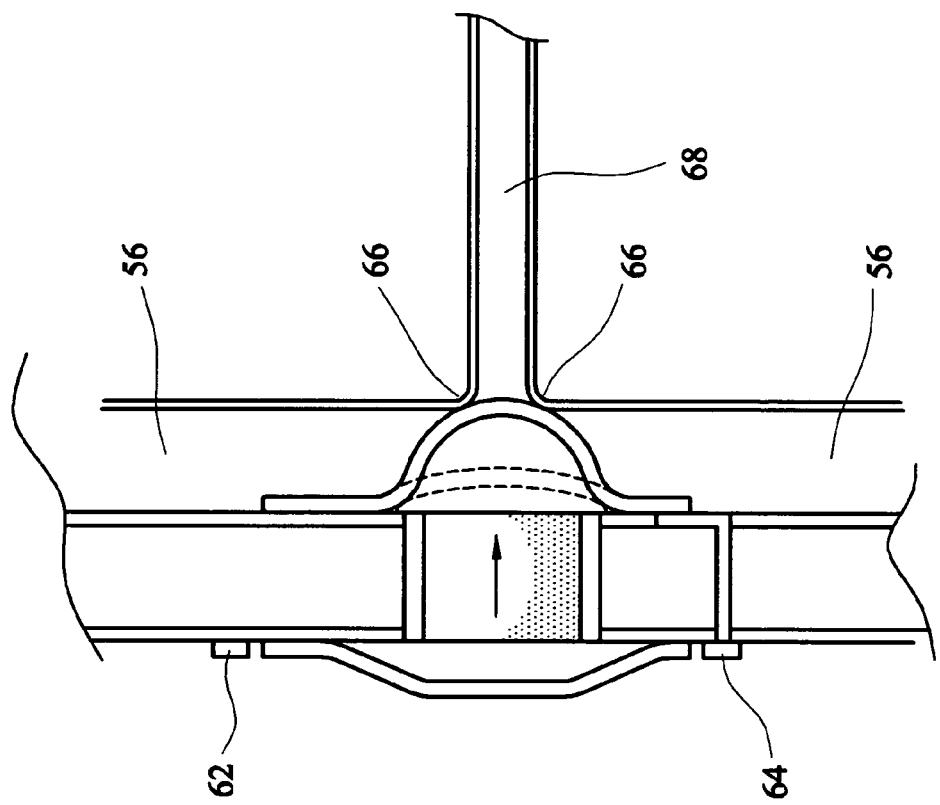
FIG. 2b is a side view of the valve shown in FIG. 2a which is closed to prevent flow of primary fluid.
Figure 2A:
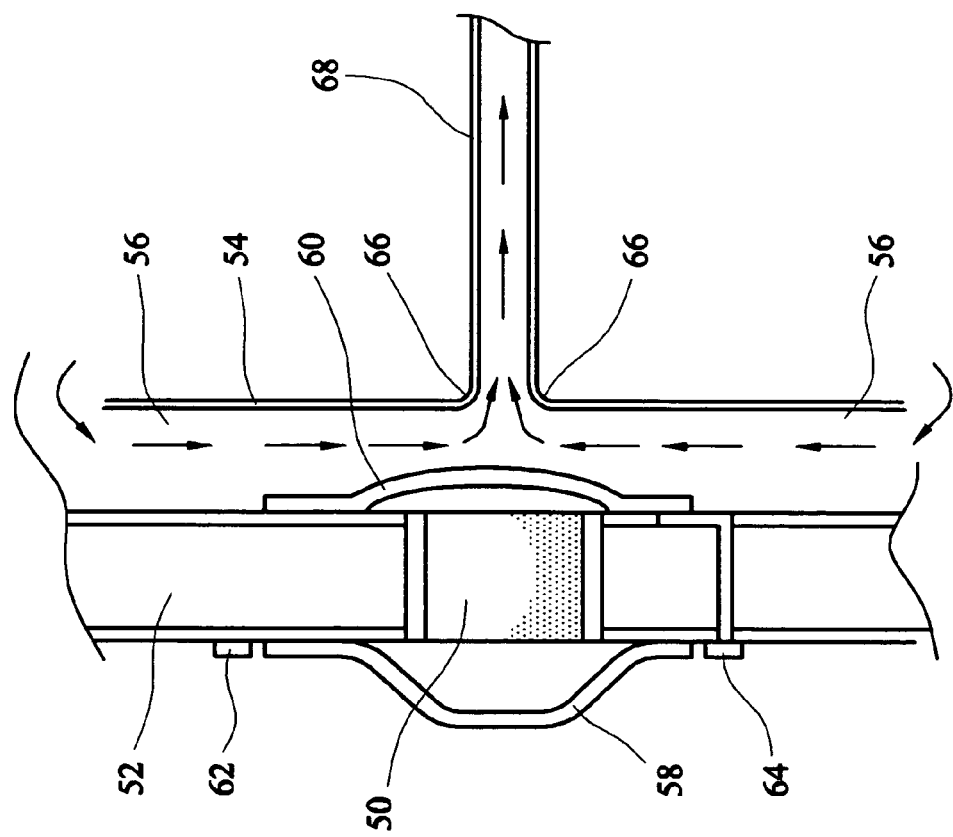
FIG. 2a is a side view of another embodiment of valve according to the invention which is open to allow flow of primary fluid.

As shown in FIG. 2a, valve fluid is located primarily on the inlet side of the membrane. Primary fluid is therefore able to flow the primary flow channel 56.

As shown in FIG. 2b, valve fluid is located predominantly in the outlet side of the membrane. This causes the membrane to swell, to contact opposite faces 66 of the flow channel. The orifice provided by the outlet limb 68 of the flow channel is closed as a result of action against it of the diaphragm seal 60.

Figure 3:
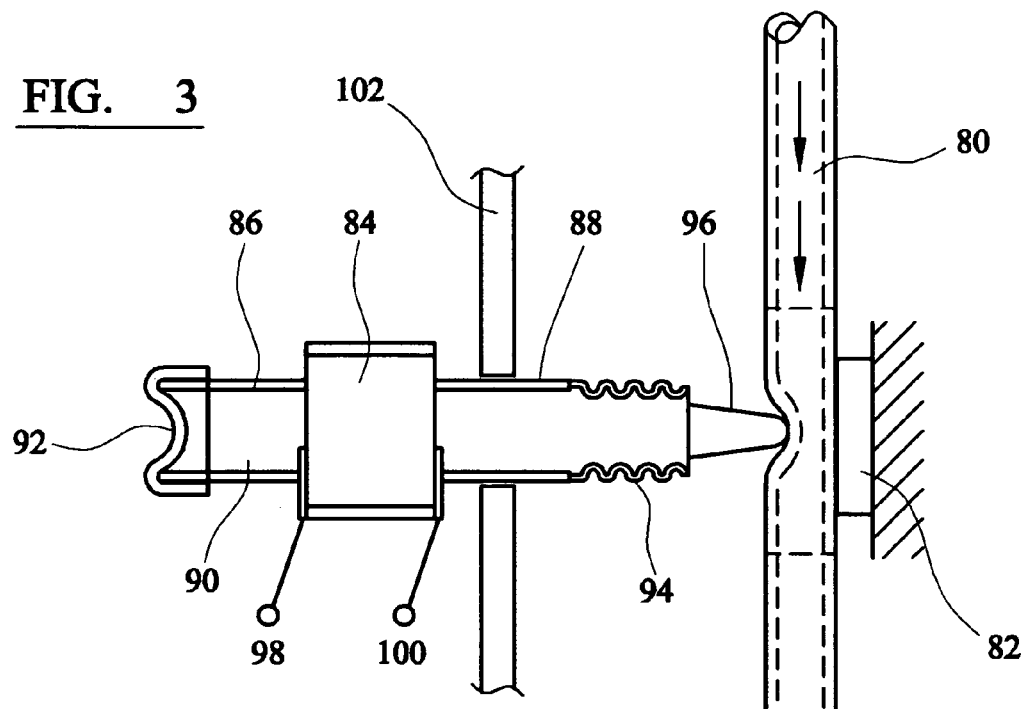
FIG. 3 is a side view of another embodiment of valve according to the invention.

FIG. 3 shows a valve for controlling flow of a primary fluid in a primary flow channel 80. The primary flow channel comprises a compressible tube. The use of compressible tubes for conducting liquids is well known, especially in medical applications. Examples of suitable materials include, for example, polyurethanes, silicones and the like. The primary flow channel is located adjacent to a support 82.

The valve includes an electro-osmotic pump which includes a membrane 84 formed to make porous dielectric material, and inlet and outlet tubes 86, 88. The membrane and the inlet and outlet tubes together form a valve fluid channel, which contains a quantity of a valve fluid 90.

The free end of the inlet tube 86 is closed by means of a flexible diaphragm seal 92. The free end of the outlet tube 88 includes a bellows 94, having a mandrel 96 attached to it at the end which faces the compressible tube 80 of the primary flow channel.

Electrodes 98, 100 are included in the valve fluid channel in contact with liquid in the inlet and outlet tubes 86, 88.

The application of a potential difference across the membrane 84 causes valve fluid to flow between the inlet and outlet tubes 86, 88. The configuration of the diaphragm seal 92 at the inlet end is able to change to accommodate the change of valve fluid in the inlet tube.

Similarly, the bellows 94 on the outlet tube 88 is able to expand to accommodate an increase in the volume of valve fluid in the outlet tube 88.

Expansion of the bellows 94 leads to movement of the mandrel 96 towards the compressible tube of the primary flow channel. Continued movement of the mandrel causes compression of the tube, leading to a reduction in the rate of flow of primary fluid.

Valve fluid can be made to flow in the reverse direction so as to withdraw the mandrel from the compressible tube, opening the primary flow channel to flow of primary fluid. This can be accomplished by reversing the polarity of the potential difference applied across the membrane 84.

The outlet tube 88 is mounted in a baffle 102. The baffle 102 is fixed spatially relative to the support 82 and the compressible tube 80 of the primary flow channel.

Figure 4:
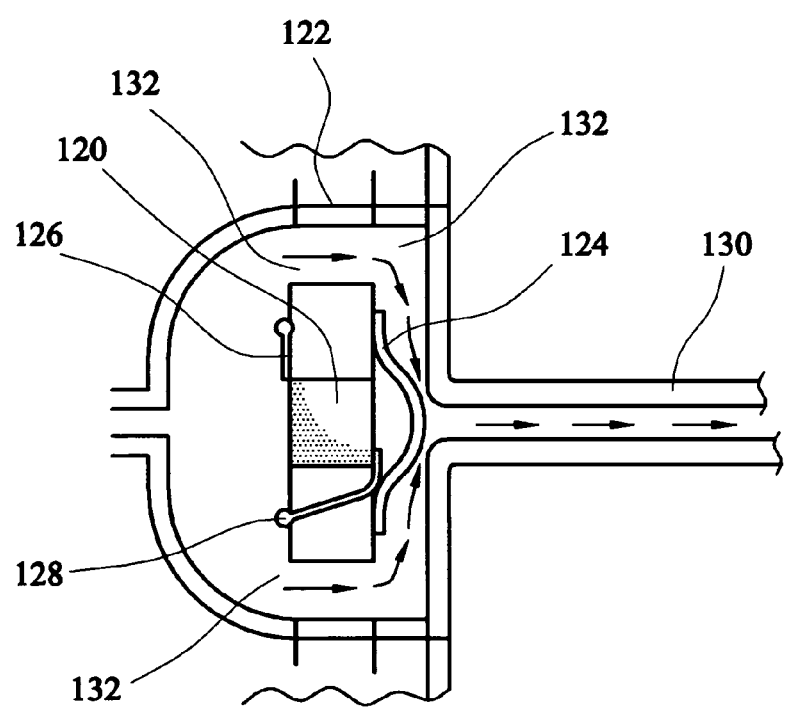
FIG. 4 is a side view of a further embodiment of valve according to the invention.

FIG. 4 shows a valve in which the valve fluid and the primary fluid are in fluid communication with one another and have the same composition. This of course requires that the primary fluid whose flow is to be controlled by the valve of the invention is capable of participating in electro-osmotic flow.

As in the valve shown in FIG. 2, the valve shown in FIG. 4 comprises a membrane 120 of a porous dielectric material which is embedded in a baffle 122. A diaphragm seal 124 is provided on the outlet side of the membrane. Electrodes 126, 128 enable a potential difference to be applied across the membrane 120.

The valve does not include a diaphragm seal on the inlet side: instead, the inlet side of the membrane is exposed to primary fluid which flows towards the primary fluid outlet 130 through openings 132 in the baffle 122.

The application of a potential difference across the membrane 120 can be relied on to cause valve fluid (which is the same as the primary fluid) to flow through the membrane into the space between the membrane and the diaphragm seal 124. The diaphragm seal is then able to close the outlet conduit 130 to prevent flow of primary fluid.

Figure 5A:
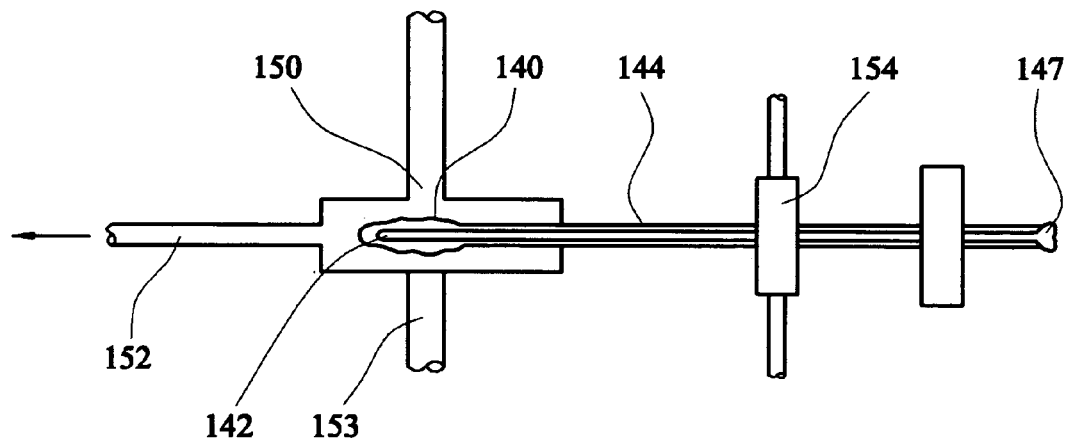
FIG. 5a is a side view of another embodiment of valve according to the invention.
Figure 5B:
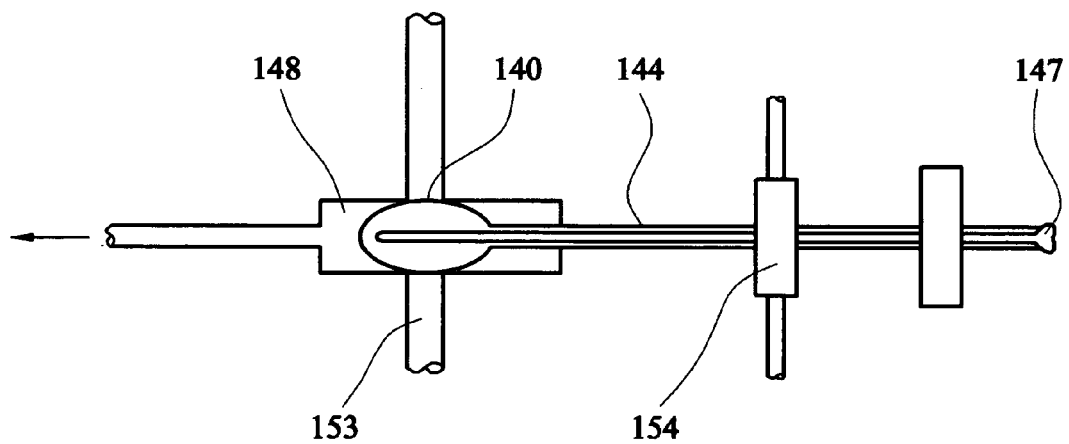
FIG. 5b is a side view of the valve shown in FIG. 5a, which is closed to prevent flow of primary fluid.

FIG. 5a shows a valve in which the valve member comprises a diaphragm 140 which is provided on the end 142 of a valve fluid channel 144. The valve fluid channel has a membrane 146 of a porous dielectric material provided in it, with associated electrodes, as discussed above. The valve fluid channel includes an expandable reservoir 147 at its inlet end. The diaphragm is located within a chamber 148 which has an inlet 150 for the primary fluid and two outlets 152, 153. As shown in FIG. 5a, the diaphragm is in its open position in which it is uninflated, where fluid is able to flow between the inlet 150 to the chamber and the two outlets. As shown in FIG. 5b, the diaphragm is in its closed position in which it is inflated (in the manner of a balloon), so that the inlet 150 and the outlet 153 are blocked by the diaphragm, preventing flow of fluid between the inlet 150 and each of the outlets 152, 153. Note that the chamber can be modified to have more than one inlet, or one or more outlets. The valve could be modified to include more than one diaphragm, or to include more than one electro-osmotic device.

As shown in FIGS. 5a and 5b, the illustrated valve includes a latching valve 154, which can be a shuttle valve of the kind described below with reference to FIGS. 8 and 9.

Figure 6:
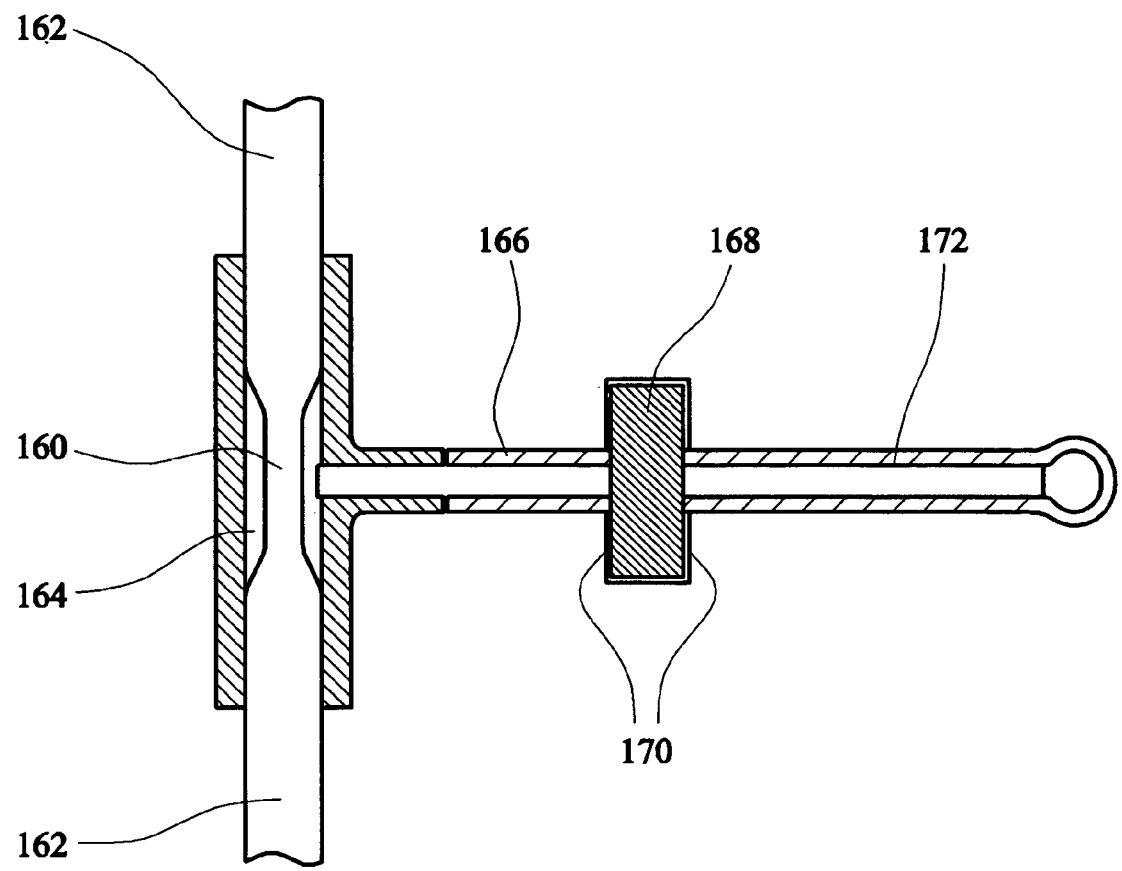
FIG. 6 is a side view of a further embodiment of valve according to the invention.

FIG. 6 shows a valve according to the invention in which the valve member comprises a compressible tube 160 which forms part of the primary flow channel 162. The compressible tube is located within a chamber 164 which is in fluid communication with the outlet part of the valve fluid channel 166. The valve fluid channel includes a membrane 168 of porous dielectric material, with associated electrodes 170, to cause fluid to flow between the outlet part of the channel and an inlet part 172. Accordingly, an increase in fluid pressure in the said chamber as a result of flow of valve fluid into the outlet part of the valve fluid channel, due to the application of a potential difference across the membrane 168 can cause compression of the compressible tube, to reduce (or to close completely) the flow of the primary fluid through the compressible tube 160.

Figure 7A:
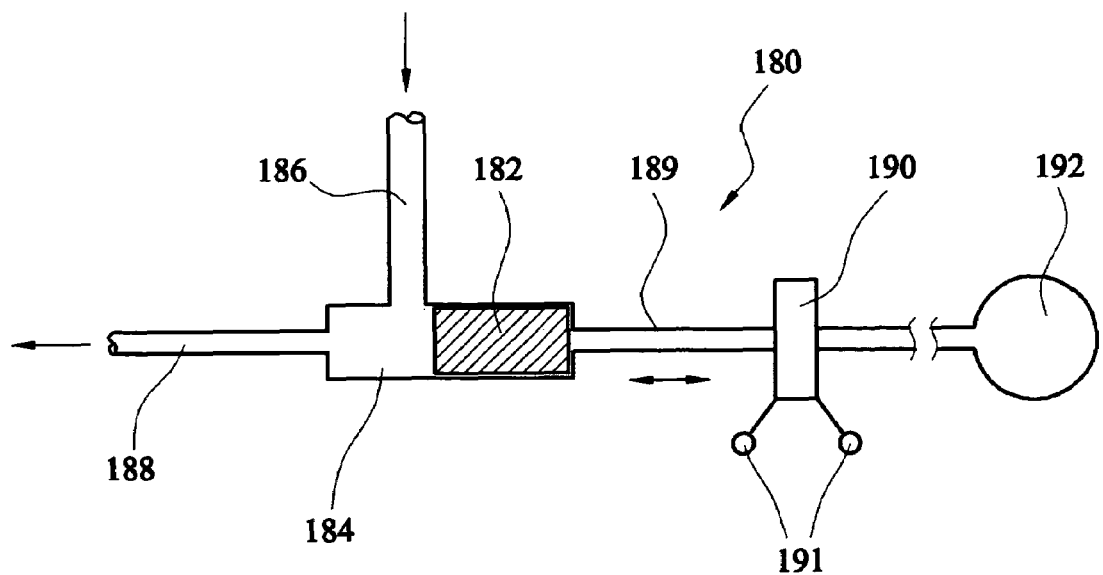
FIG. 7a is a side view of a shuttle valve according to the invention, with the shuttle valve member in the open position.
Figure 7B:
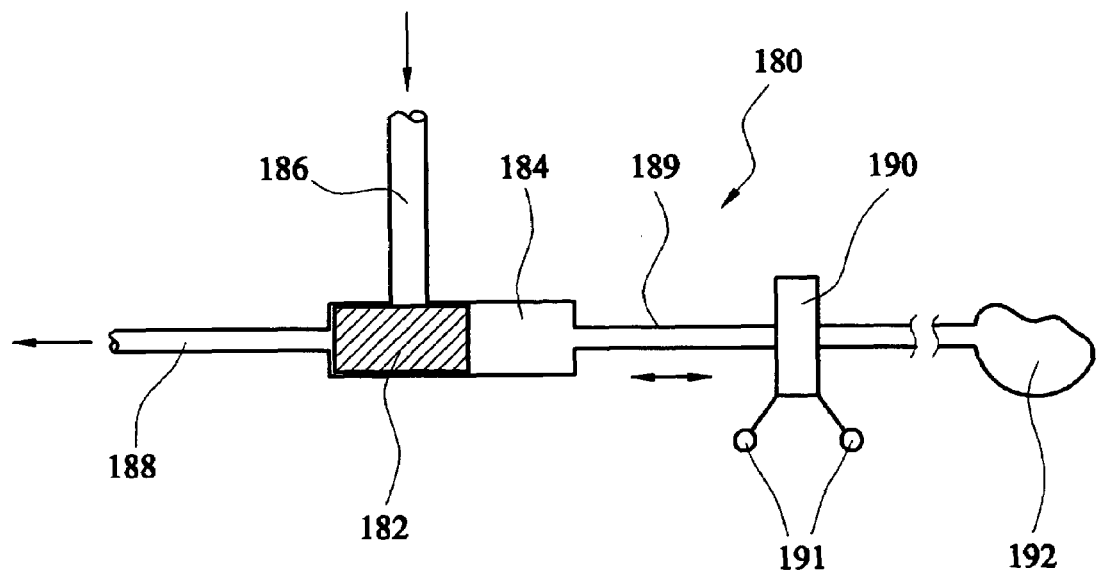
FIG. 7b is a side view of the shuttle valve member of the valve shown in FIG. 7a, in the closed position.

FIG. 7a shows a valve 180 which comprises a valve member 182 which can slide within a chamber 184 which defines a valve member housing. The chamber has an inlet 186 and an outlet 188 for the primary fluid. The chamber is in communication with the outlet part 189 of the valve fluid channel, which contains a membrane 190 of a porous dielectric material and associated electrodes 191. The valve fluid channel includes a resiliently expandable reservoir 192 for valve fluid at its inlet end. The valve member is able to slide between its open position as shown in FIG. 7a in which the inlet 186 is open, allowing fluid to flow through the chamber from the inlet 186 to the outlet 188, to the closed position as shown in FIG. 7b in which the inlet 186 is closed. With appropriate fine control of the position of the valve member, the inlet can be closed partially by locating the valve member so that it only partially covers the inlet.

Figure 8A:
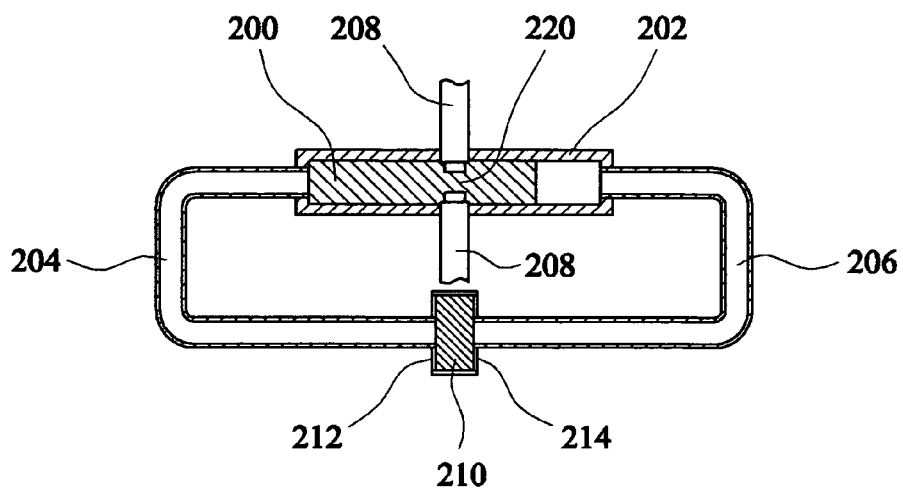
FIG. 8a is a side view of another embodiment of shuttle valve according to the invention, with the shuttle valve member in the open position.
Figure 8B:
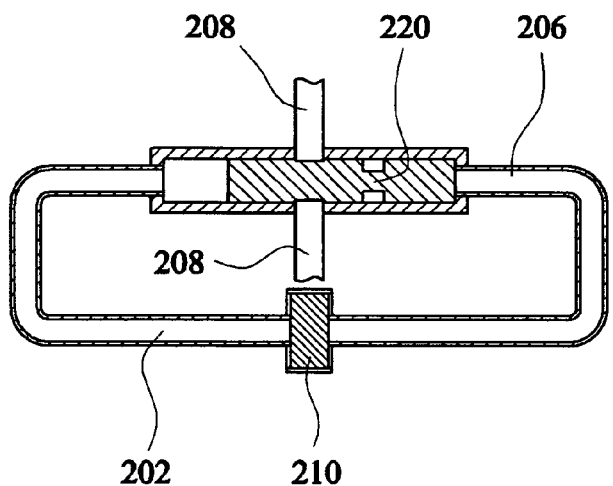
FIG. 8b is a side view of the shuttle valve member of the valve shown in FIG. 8a, in the closed position.
Figure 9:
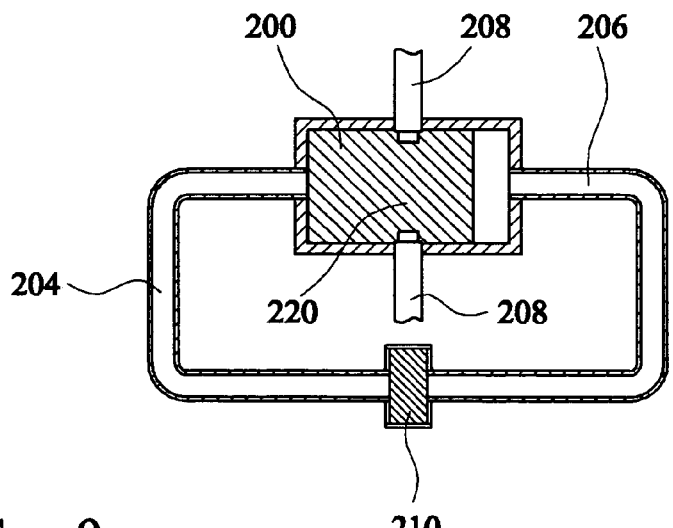
FIG. 9 is a side view of another embodiment of shuttle valve.

FIGS. 8 and 9 relate to a construction of valve in which valve fluid on both the inlet and outlet sides of a membrane acts on a valve member, which can move in a reciprocating (or shuttle) action in a valve member housing.

The valve shown in FIG. 8a includes a shuttle valve member 200 which is able to slide within a valve member housing 202. The valve member housing is moulded from a polycarbonate material. The shuttle valve member is made from stainless steel. The valve member housing is connected at each of its opposite ends to the inlet and outlet tubes 204, 206 of an electro-osmotic flow device of the kind described above. The valve is used to control flow of primary fluid through a primary flow channel which is defined by a tube 208 which communicates with the interior of the valve member housing 202.

The valve shown in FIG. 8a includes a membrane 210 which has electrodes in contact with valve fluid in the inlet and outlet tubes 204, 206. Application of a potential difference across the membrane 210 causes migration of valve fluid across the membrane 210, changing the relative amounts of the valve fluid in the inlet and outlet tubes 204, 206. This change in the distribution of the valve fluid is accommodated by movement of the shuttle valve member 200 within the valve member housing 202.

The shuttle valve member has a cylindrical form with a round cross-section, and is a close sliding fit within the valve member housing. A portion 220 of the shuttle valve member has a reduced diameter so that there is an annular space in that region of the shuttle valve member, between its external surface and the internal surface of the valve member housing. The distance of this reduced diameter portion from the end of the shuttle valve member is the same as the distance from one end of the valve member housing to the primary flow channel 208. Accordingly, when the shuttle valve member is at the limit of its movement in one direction within the valve member housing, the reduced diameter portion 220 is aligned with the primary flow channel, allowing the primary fluid in the primary flow channel to flow around the shuttle valve member, through the valve member housing. In another embodiment, the shuttle valve member can have an opening extending through it in the form of a bore, which is aligned with the primary flow channel when the valve member is in its open position.

Movement of valve fluid from the outlet tube 206 to the inlet tube 204, through the membrane 210, causes the shuttle to move from the open configuration shown in FIG. 7a towards the closed configuration shown in FIG. 7b. As shown in FIG. 7b, the reduced diameter portion 220 is displaced relative to the flow channel 208, shutting the flow channel 208 against flow of primary fluids.

The embodiment of the shuttle valve member and valve member housing shown in FIG. 9 has different dimensions. The cross-sectional area of the shuttle valve member is larger. The distance through which it moves (represented by the free space between the end of the shuttle valve member and the valve member housing) is smaller. The length of the reduced diameter portion 220 of the shuttle valve member is less. This construction of valve member and housing enables larger forces to be generated to move the shuttle valve member within the housing.

A composite valve according to the invention can comprise a primary valve which is used to control the flow of the primary fluid, as discussed above: certain primary valve constructions (for example as shown in FIGS. 1 to 7 above) are susceptible to reverting from the closed configuration towards or to the open configuration due to pressure of fluid in the primary flow channel. It can be desirable to latch the primary valve in its open position or in its closed position. This can be achieved by means of a latching valve. A shuttle valve such as those shown in FIGS. 8 and 9 can be used as a latching valve in a composite valve. When a shuttle valve is used as a latching valve, the primary fluid for the purposes of the shuttle valve is the valve fluid for the primary valve, so that moving the shuttle valve between open and closed positions allows flow of the valve fluid for the primary valve to flow in the respective valve fluid channel, to move the valve member to close or to open the valve. However, the flow of this valve fluid is only possible when the shuttle latching valve is open.

Accordingly, a shuttle valve, for example as shown in FIG. 8 or FIG. 9, can be incorporated with a primary valve, for example as shown in any of FIGS. 1 to 7, to form a composite valve.

Figure 10:
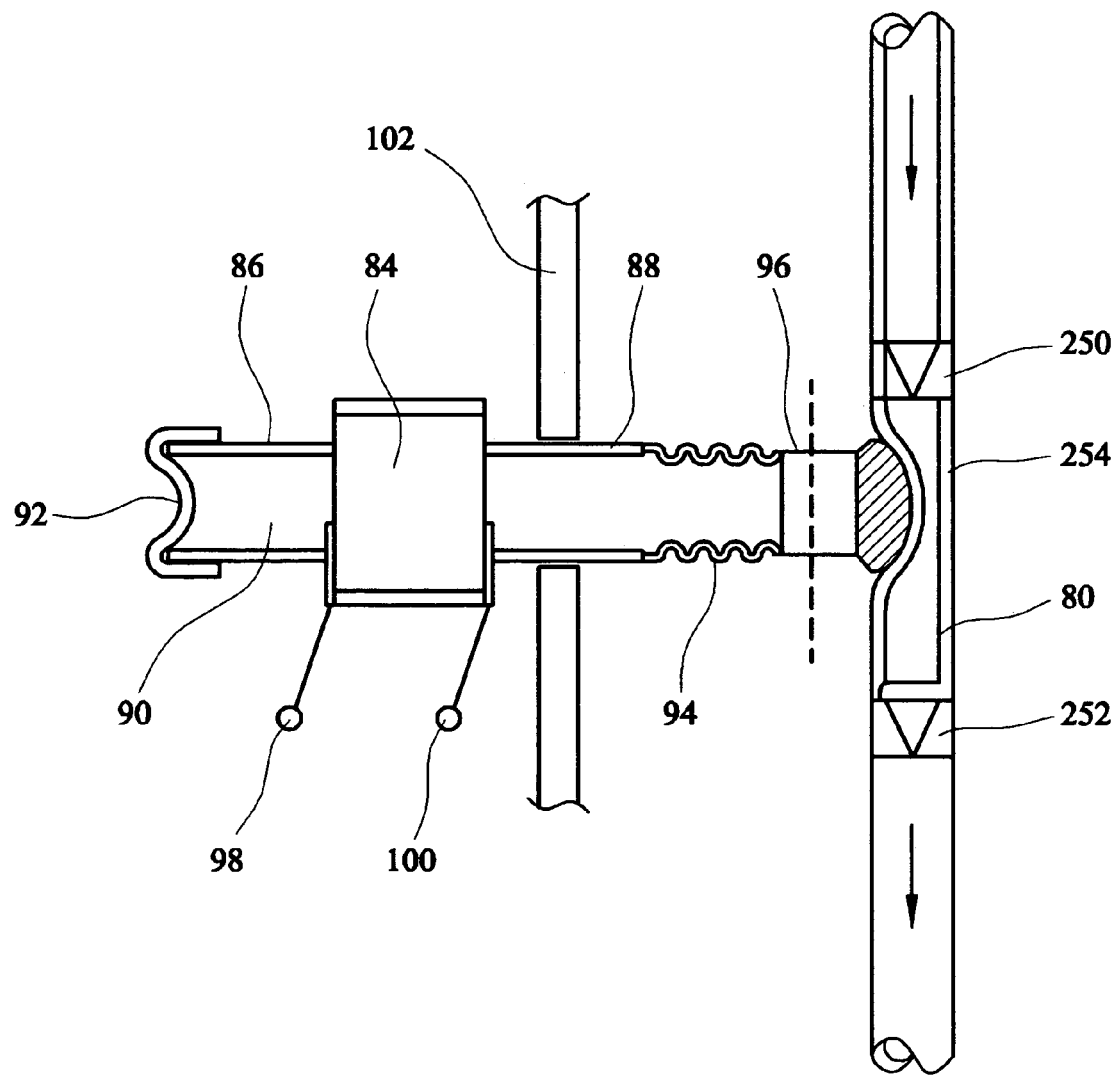
FIG. 10 is a side view of a pump which incorporates a valve according to the invention.

FIG. 10 shows a pump construction which is based on the valve shown in FIG. 3. All of the features of the valve fluid channel and the deformable diaphragm and bellows are as described above in relation to FIG. 3.

The compressible tube 80 includes a first one-way flow valve 250 which is located upstream of the mandrel 96, and a second one-way flow valve 252 which is located downstream of the mandrel 96. This valve assembly can be used to pump fluid. When the space 254 between the one-way valves 250, 252 is full of primary fluid, the valve fluid can be pumped into the outlet tube 88, causing the mandrel 96 to compress the tube. The one-way valve 250 remains closed as the tube is compressed, and the one-way valve 252 opens, allowing primary fluid in the space 254 to be ejected from that space.

When the potential difference across the membrane 84 is reversed so that the mandrel is withdrawn, the volume of the space 254 in the compressible tube increases. This draws primary fluid into the said space. Valve 252 closes and valve 250 opens.

Repeated movement of the mandrel 96, inwardly and outwardly relative to the compressible tube 80, causes controlled quantities of the primary fluid to be discharged repeatedly from the compressible tube 80.

Figure 11A:
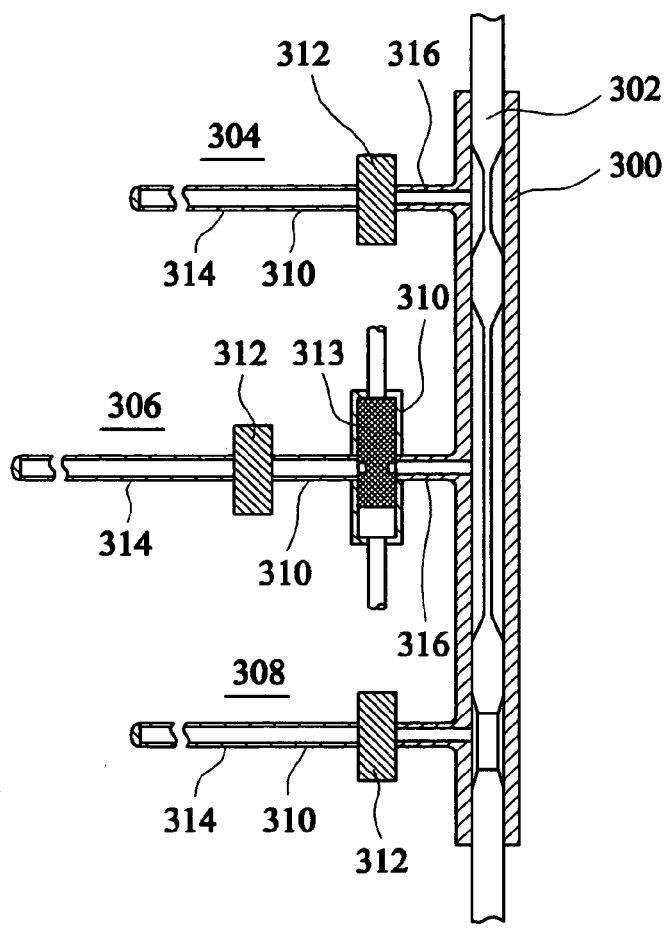
FIG. 11a is a side view of another embodiment of pump.
Figure 11B:
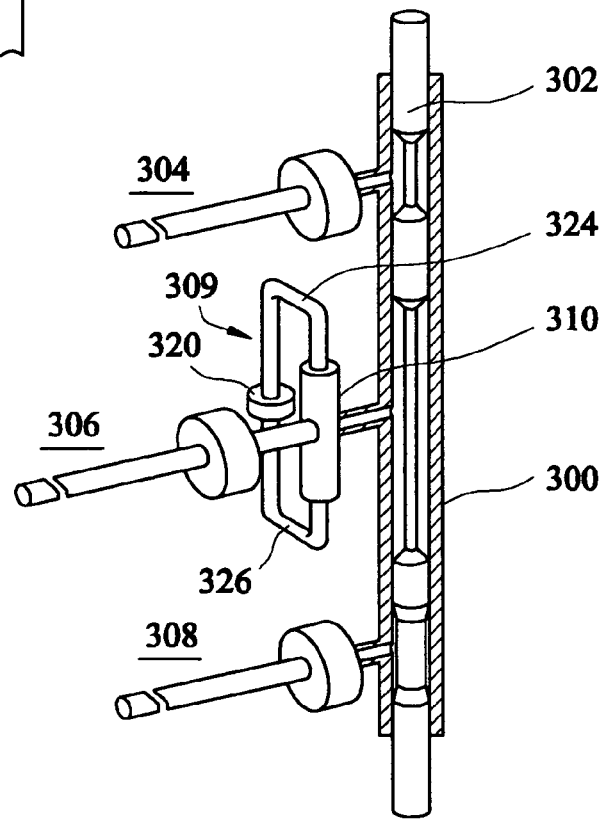

FIGS. 11a and 11b show a pump which comprises a tubular housing 300 which contains a flow channel 302 for a primary fluid. The flow channel is provided within the housing 300 by a compressible tube. The tube can be compressed in three axially spaced regions of the housing.

The pump includes three valves 304, 306, 308 of the kind discussed generally above, arranged along the housing. Each of them comprises a valve fluid channel 310 containing a membrane 312 of a porous dielectric material, and having an inlet end 314 with a reservoir for the valve fluid, and an outlet end 316 which communicates with the housing 300. Each of the valves 304, 306, 308 can be operated in the manner of the valve shown in FIG. 6. When each of the valves is in the open configuration, its valve fluid is biased towards the inlet end of the valve fluid channel. When each of the valves is in the closed configuration, its valve fluid is biased towards the outlet end of valve fluid channel. It then compresses the compressible tube 302 within the housing 300 in one of the spaced apart regions thereof in which the tube can be compressed.

The central one 306 of the three valves includes a shuttle latching valve 309. The latching valve a shuttle valve member 310 which is able to slide within a valve member housing 313. The valve member housing is moulded from a polycarbonate material. The shuttle valve member is made from stainless steel. The valve member housing is connected at each of its opposite ends to the inlet and outlet tubes 324, 326 of an electro-osmotic flow device of the kind described above. The valve is used to control flow of the valve fluid of the central valve 306 through the respective channel 310, which communicates with the interior of the tubular housing 300, in which the valve member provided by the compressible tube 302 is located.

The shuttle latching valve includes a membrane 320 which has electrodes in contact with valve fluid in the inlet and outlet tubes 324, 326. Application of a potential difference across the membrane 320 causes migration of valve fluid across the membrane, changing the relative amounts of the valve fluid in the inlet and outlet tubes 324, 326. This change in the distribution of the valve fluid is accommodated by movement of the shuttle valve member 310 within the valve member housing 313.

The pump shown in FIGS. 11a and 11b is operated cyclically. Initially, all three of the valves 304, 306, 308 are in their closed positions, with the compressible tube 302 within the housing 300 compressed in each of the spaced apart regions thereof in which the tube can be compressed.

The upper valve 304 is then opened to admit flow of the primary fluid, and the central valve 306 is then opened to admit the primary fluid into the compressible tube 302, in the central region of the housing 300. The upper valve 304 is then closed to prevent flow of primary fluid. The lower valve 308 is then opened, and the central valve closed. Closing the central valve causes fluid in the compressible tube 302, in the central region of the housing 300, to be expelled from the compressible tube.

The latching valve which forms part of the central valve 306 can be relied on to latch the central valve in its open position or its closed position as required. Similar latching valves can be incorporated with one or both of the upper and lower valves 304, 308.

With any two of the valves 304, 306, 308 of the pump in their open positions, the third valve can be used to control the flow of the primary fluid.

The invention claimed is:

1. A valve for controlling flow of a primary fluid in a primary flow channel which comprises
   a) a valve fluid channel;
   b) a membrane of a porous dielectric material located in the valve fluid channel so as to divide the valve fluid channel into an inlet part and an outlet part and so that valve fluid flowing between the inlet and outlet parts flows through the said membrane;
   c) first and second electrodes located for electrical communication with valve fluid in the inlet and outlet parts respectively of the valve fluid channel for application of an electric potential across the membrane in order to promote electro-osmotic flow of valve fluid through the membrane;
   d) the outlet part of the valve fluid channel being located at least partially within the primary flow channel, at least part of the wall of the outlet part of the valve fluid channel comprising a valve member being a tubular part for expandable diaphragm sleeve, the tubular diaphragm sleeve can be displaced between open and closed positions as a result of valve fluid moving in the valve fluid channel through the membrane into or out of the outlet part of the valve fluid channel so that an increase in fluid pressure in the outlet part of the valve fluid channel causes the tubular diaphragm to expand transversely relative to the valve fluid channel towards the wall of the primary flow channel to cause a reduction in the capacity for flow of the primary fluid in the primary flow channel when it is in the closed position compared with when it is in the open position.

2. A valve as claimed in claim 1 further comprising a latching valve to control flow of the valve fluid in the valve fluid channel.

3. A valve as claimed in claim 2 wherein the latching valve is a shuttle valve.

4. A valve as claimed in claim 3 wherein the shuttle valve comprises a shuttle valve member adapted to slide within a shuttle valve member housing to control fluid flow through the housing between input and output ports in the housing.

5. A valve as claimed claim 1, wherein the diaphragm is a resiliently deformable material.

6. A valve as claimed in claim 1, wherein the inlet part of the valve fluid channel comprises a resiliently expandable reservoir.

7. A valve for controlling flow of a primary fluid in a primary flow channel which comprises
   a) a valve fluid channel;
   b) a membrane of a porous dielectric material located in the channel so as to divide the channel into an inlet part and an outlet part and so that the valve fluid flowing between the inlet and outlet parts flows through the said membrane;
   c) first and second electrodes located for electrical communication with valve fluid in the inlet and outlet parts respectively of the valve fluid channel for application of an electric potential across the membrane in order to promote electro-osmotic flow of valve fluid through the membrane;
   d) a valve member which can be displaced between open and closed positions as a result of valve fluid moving in the valve fluid channel through the membrane, into or out of the outlet part of the valve fluid channel, in which the valve member causes a reduction in the capacity for flow of the primary fluid in the primary flow channel when it is in the closed position compared with when it is in the open position; the valve member comprising a compressible tube which forms part of the primary flow channel, the compressible tube being located within a chamber which is in fluid communication with the outlet part of the valve fluid channel so that an increase in fluid pressure in the said chamber as a result of flow of valve fluid into the outlet part of the valve fluid channel can cause compression of the compressible tube, to reduce the flow of the primary fluid through the compressible tube.

8. A valve as claimed in claim 7, wherein the compressible tube is compressed circumferentially by the valve fluid.

9. A valve for controlling flow of a primary fluid in a primary flow channel which comprises:
   a) a valve fluid channel;
   b) a membrane of a porous dielectric material located in the channel so as to divide the channel into an inlet part and an outlet part and so that valve fluid flowing between the inlet and outlet parts flows through the said membrane;
   c) first and second electrodes located for electrical communication with valve fluid in the inlet and outlet parts respectively of the valve fluid channel for application of an electric potential across the membrane in order to promote electro-osmotic flow of valve fluid through the membrane;
   d) a valve member which can be displaced between open and closed positions as a result of valve fluid moving in the valve fluid channel through the membrane, into or out of the outlet part of the valve fluid channel, in which the valve member causes a reduction in the capacity for flow of the primary fluid in the primary flow channel when it is in the closed position compared with when it is in the open position;
   e) a valve member housing in which the valve member can move between the said open and closed positions; the valve member housing having a first end towards which the valve member moves when moving towards its open position from its closed position and an opposite second end towards which the valve member moves when moving towards its closed position from its open position, and in which the valve member housing has a first opening at or towards the first end thereof which communicates with the inlet part of the valve fluid channel and a second opening at or towards the second end thereof which communicates with the outlet part of the valve fluid channel.

10. A pump for controlling flow of a primary fluid in a primary flow channel which comprises
   a) a driver valve comprising:
      i) a valve fluid channel;
      ii) a membrane of a porous dielectric material located in the channel so as to divide the channel into an inlet part and an outlet part and so that the valve fluid flowing between the inlet and outlet parts flows through the said membrane;
      iii) first and second electrodes located for electrical communication with valve fluid in the inlet and outlet parts respectively of the valve fluid channel for application of an electric potential across the membrane in order to promote electro-osmotic flow of valve fluid through the membrane;
      iv) a valve member which can be displaced between open and closed positions as a result of valve fluid moving in the valve fluid channel through the membrane, into or out of the outlet part of the valve fluid channel, in which the valve member causes a reduction in the volume of the primary flow channel when it is in the closed position compared with when it is in the open position;
   b) an inlet valve located upstream of the driver valve for controlling flow of primary fluid into the primary flow channel when it is acted on by the driver valve; and
   c) an outlet valve located downstream of the driver valve for controlling release of primary fluid from the primary flow channel when it is acted on by the driver valve; the pump further comprising a latching valve to control flow of the valve fluid in the valve fluid channel.

11. A pump as claimed in claim 10, wherein the latching valve comprises a latching valve member housing towards which a latching valve member moves when moving towards its open position from its closed position and an opposite second end towards which the latching valve member moves when moving towards its closed position from its open position, and in which the latching valve member housing comprises a first opening at or towards the first end thereof which communicates with an inlet part of a second valve fluid channel and a second opening at or towards the second end thereof which communicates with an outlet part of the second valve fluid channel.

12. A pump as claimed in claim 11, wherein the inlet and outlet parts of the second fluid channel are separated by a membrane comprising a porous dielectric material.

13. A pump as claimed in claim 12, further comprising third and fourth electrodes located for electrical communication with the valve fluid in the inlet and outlet parts of the second valve fluid channel respectively for application of an electric potential across the membrane in order to promote electro-osmotic flow of valve fluid through the membrane.

14. A pump for controlling flow of a primary fluid in a primary flow channel, which comprises
   a) a driver valve comprising:
      i) a valve fluid channel;
      ii) a membrane of a porous dielectric material located in the channel so as to divide the channel into an inlet part and an outlet part and so that the valve fluid flowing between the inlet and outlet parts flows through the said membrane;
      iii) first and second electrodes located for electrical communication with valve fluid in the inlet and outlet parts respectively of the valve fluid channel for application of an electric potential across the membrane in order to promote electro-osmotic flow of valve fluid through the membrane;
      iv) a valve member which can be displaced between open and closed positions as a result of valve fluid moving in the valve fluid channel through the membrane, into or out of the outlet part of the valve fluid channel, in which the valve member causes a reduction in the volume of the primary flow channel when it is in the closed position compared with when it is in the open position;
   b) an inlet valve located upstream of the driver valve for controlling flow of primary flow into the primary flow channel when it is acted on by the driver valve; and c) an outlet valve located downstream of the driver valve for controlling release of primary fluid from the primary flow channel when it is acted on by the driver valve the valve member comprising a compressible tube which forms part of the primary flow channel, the compressible tube being located within a chamber which is the fluid communication within the outlet part of the valve fluid, channel such that an increase in fluid pressure in the said chamber as a result of flow of valve fluid into the outlet part of the valve fluid channel can cause compression of the compressible tube to reduce the flow of the primary fluid through the compressible tube.

15. A pump as claimed in claim 14, wherein the compressible tube is compressed circumferentially by the valve fluid.

* * * * *